United States Patent
Gessert et al.

(10) Patent No.: US 7,155,957 B2
(45) Date of Patent: Jan. 2, 2007

(54) APPARATUS AND METHODS FOR TESTING ACOUSTIC PROBES AND SYSTEMS

(75) Inventors: James M. Gessert, Colorado Springs, CO (US); William H. Phillips, Jr., Samamish, WA (US); G. Wayne Moore, Lyons, CO (US)

(73) Assignee: Sonora Medical Systems, Inc., Longmont, CO (US)

( * ) Notice: Subject to any disclaimer, the term of this patent is extended or adjusted under 35 U.S.C. 154(b) by 0 days.

(21) Appl. No.: 11/319,921

(22) Filed: Dec. 27, 2005

(65) Prior Publication Data

US 2006/0101896 A1    May 18, 2006

Related U.S. Application Data

(62) Division of application No. 10/426,137, filed on Apr. 28, 2003, now Pat. No. 7,028,529.

(51) Int. Cl.
*G01N 29/30* (2006.01)
*G01R 27/26* (2006.01)

(52) U.S. Cl. ........................................ 73/1.82; 324/686
(58) Field of Classification Search ................. 73/1.82; 702/116; 367/13; 381/58; 324/686
See application file for complete search history.

(56) References Cited

U.S. PATENT DOCUMENTS 7,007,539 B1 *   3/2006   Gessert et al. ............... 73/1.82

FOREIGN PATENT DOCUMENTS

SU              558424 A      6/1977

OTHER PUBLICATIONS

Sonora Medical Systems Press Release entitled "Longmont, CO: Sonora Medical Systems Introduces First Automated Ultrasound Transducer Test Device," Jun. 16, 2001; 2 pages.
Sonora Medical Systems, Technical Notes entitled "Understanding the FirstCall2000™ Measured Parameters," Nov. 2002, 1 page 2 pages.
Weigang, B. et al., "The Methods and Effects of Transducer Degradation on Image Quality and the Clinical Efficacy of Diagnostic Sonography," JDMS, Jan./Feb. 2003, pp. 3-13, vol. 19, No. 1.

* cited by examiner

*Primary Examiner*—Thomas P. Noland
(74) *Attorney, Agent, or Firm*—Townsend and Townsend and Crew LLP

(57) ABSTRACT

Methods and apparatus are provided for testing an acoustic device that has multiple transducing elements adapted for conversion between acoustic and electrical signals. An electrical transmission signal is generated. The electrical transmission signal is transmitted to a selected transducing element. An electrical received signal is received from the acoustic device. A reference signal is generated. A capacitance associated with the selected transducing element is determined from the reference signal. Operational characteristics of the selected transducing element are diagnosed from the determined capacitance and the electrical received signal.

12 Claims, 8 Drawing Sheets

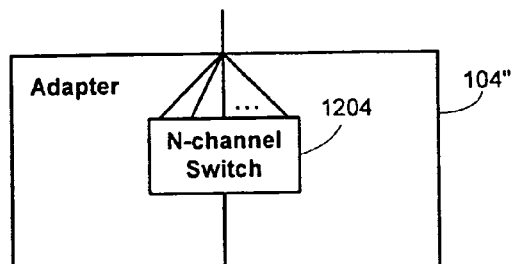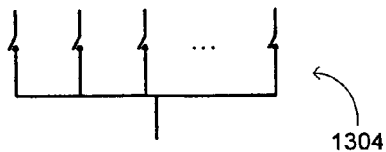
Fig. 13A
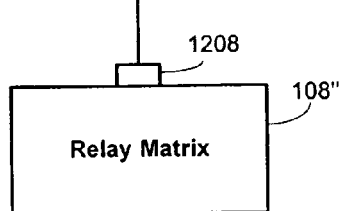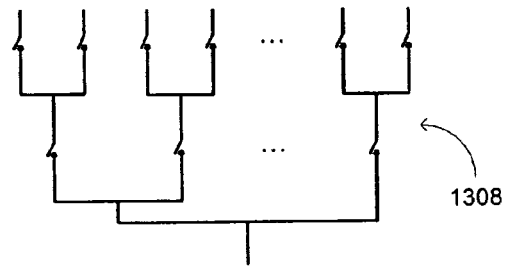
Fig. 12
Fig. 13B
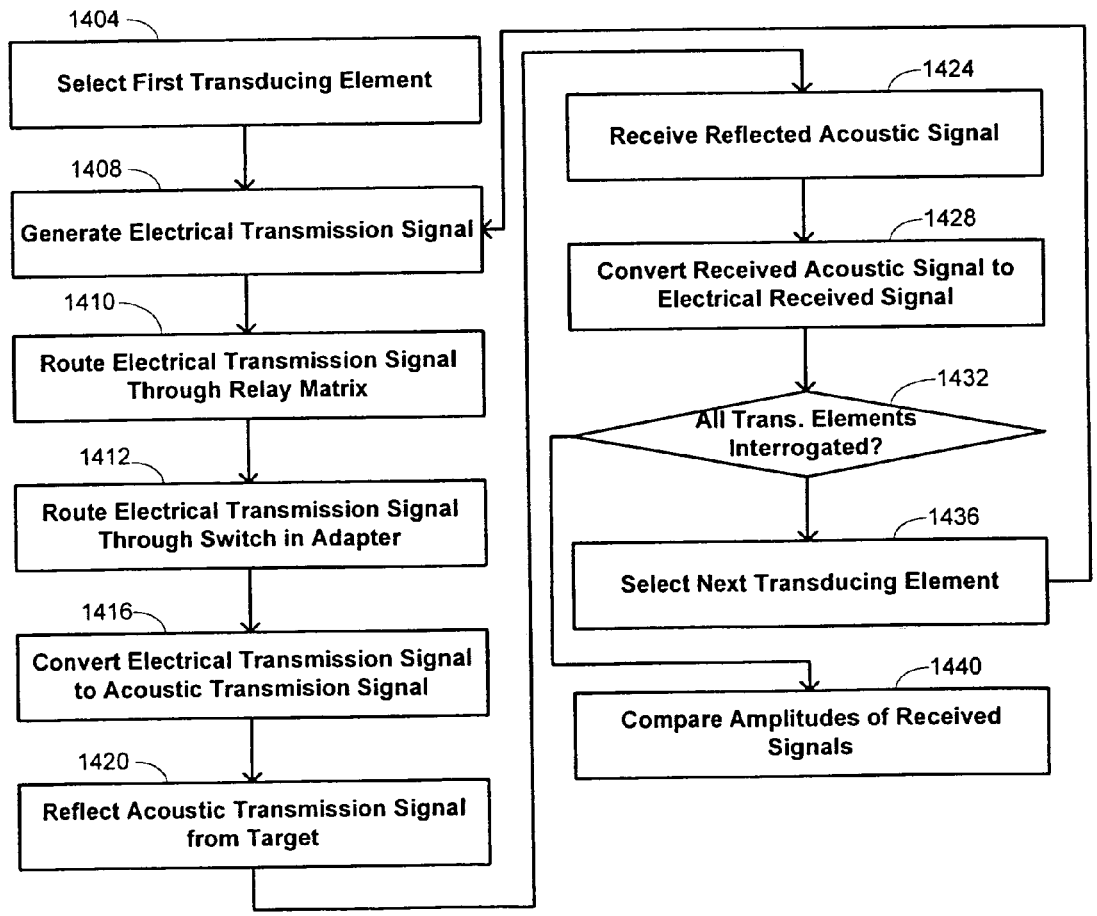
Fig. 14

APPARATUS AND METHODS FOR TESTING ACOUSTIC PROBES AND SYSTEMS

CROSS-REFERENCES TO RELATED APPLICATIONS

This application is a divisional of U.S. patent application Ser. No. 10/426,137, entitled "APPARATUS AND METHODS FOR TESTING ACOUSTIC PROBES AND SYSTEM," filed Apr. 28, 2003, now U.S. Pat. No. 7,028,529 the entire disclosure of which is herein incorporated by reference for all purposes. This application is also related to the following commonly assigned U.S. Patent applications, the entire disclosure of each of which is incorporated herein by reference in its entirety: U.S. patent application Ser. No. 10/426,156, entitled "APPARATUS AND METHODS FOR TESTING ACOUSTIC SYSTEMS," filed Apr. 28, 2003 by James M. Gessert et al. and U.S. patent application Ser. No. 10/426,066, entitled "APPARATUS AND METHODS FOR INTERFACING ACOUSTIC TESTING APPARATUS WITH ACOUSTIC PROBES AND METHODS," filed Apr. 28, 2003 by James M. Gessert et al.

BACKGROUND OF THE INVENTION

This application relates generally to acoustic probes and systems. More specifically, this application relates to apparatus and methods for testing acoustic probes and systems.

Acoustic imaging techniques have been found to be extremely valuable in a variety of applications. While medical applications in the form of ultrasound imaging are perhaps the most well known, acoustic techniques are more generally used at a variety of different acoustic frequencies for imaging a variety of different phenomena. For example, acoustic imaging techniques may be used for the identification of structural defects, for detection of impurities, as well as for the detection of tissue abnormalities in living bodies. All such techniques rely generally on the fact that different structures, whether they be cancerous lesions in a body or defects in an airplane wing, have different acoustic impedances. When acoustic radiation is incident on an acoustic interface, such as where the acoustic impedance changes discontinuously, it may be scattered in ways that permit characterization of the interface. Radiation reflected by the interface is most commonly detected in such applications, but transmitted radiation is also used for such analysis in some applications.

Transmission of the acoustic radiation towards a target and receipt of the scattered radiation may be performed and/or coordinated with a modern acoustic imaging system. Many modern such systems are based on multiple-element array transducers that may have linear, curved-linear, phased-array, or similar characteristics. These transducers may, for example, form part of an acoustic probe. In some instances, the imaging systems are equipped with internal self-diagnostic capabilities that allow limited verification of system operation, but do not generally provide effective diagnosis of the transmission and receiving elements themselves. Degradation in performance of these elements is often subtle and occurs as a result of extended transducer use and/or through user abuse. Acoustic imaging devices therefore often lack any direct quantitative method for evaluating either system or probe performance. Users and technical support personnel thus sometimes use phantoms that mimic characteristics of the object under study to provide a qualitative method for evaluating image quality and to perform a differential diagnosis between the system and the transducer array, but this technique is widely recognized to be of limited utility.

There is, therefore, a general need in the art for apparatus and methods for testing acoustic probes and systems.

BRIEF SUMMARY OF THE INVENTION

In embodiments of the invention, a method is provided for testing an acoustic device that has a plurality of transducing elements adapted for conversion between acoustic and electrical signals. An electrical transmission signal is generated. The electrical transmission signal is transmitted to a selected transducing element. An electrical received signal is received from the acoustic device. A reference signal is generated. A capacitance associated with the selected transducing element is determined from the reference signal. Operational characteristics of the selected transducing element are diagnosed from the determined capacitance and the electrical received signal.

The electrical received signal may correspond to an acoustic signal converted from the electrical transmission signal and reflected from a target. The electrical transmission signal may comprise a voltage pulse. In one embodiment, transmitting the electrical transmission signal comprises routing the electrical transmission signal through a relay element configured for selective routing from a channel to a plurality of channels. The electrical transmission signal may be further routed through an adapter having a multichannel switch.

The reference signal may comprise a linear voltage ramp. In one embodiment, the selected transducing element comprises a piezoelectric crystal and the reference signal is generated with a frequency less than a resonant frequency of the piezoelectric crystal. For example, the reference signal may have a frequency less than 100 kHz or may have a frequency less than 10 kHz. In another embodiment, the resonant frequency of the piezoelectric crystal is between 2 and 10 MHz and the reference signal has a frequency between 0.5 and 1.5 MHz.

The capacitance information provides various diagnostic capabilities. For example, in one embodiment, the selected transducing element comprises a cable connection and the capacitance derives at least in part from a cable capacitance of the cable connection. Diagnosing the operational characteristics comprises determining that the capacitance arising from the cable capacitance is a fraction of an expected value. In another embodiment, diagnosis comprises determining that an amplitude of the electrical received signal is substantially zero and determining whether the capacitance is consistent with an expected value.

These methods may be embodied on apparatus for testing the acoustic device. A transmitter may be provided to generate the electrical transmission signal. A relay element may be provided to route the electrical transmission signal to the selected transducing element. A receiver may be provided to receive the electrical received signal from the acoustic device. A waveform generator may be provided to generate the reference signal with which the capacitance associated with the selected transducing element is determined. In addition, in some embodiments, a computational unit may be provided to diagnose the operation characteristics of the selected transducing element from the determined capacitance and the electrical received signal. In other embodiments, an adapter may be provided to interface between the relay element and the transducing elements, the adapter having a multichannel switch.

The methods of the invention may also be embodied in a computer-readable storage medium having a computer-readable program embodied therein for directing operation of the apparatus. The computer-readable program includes instructions for operating the apparatus to test an acoustic device in accordance with the embodiments described above.

BRIEF DESCRIPTION OF THE DRAWINGS

A further understanding of the nature and advantages of the present invention may be realized by reference to the remaining portions of the specification and the drawings wherein like reference numerals are used throughout the several drawings to refer to similar components.

FIG. 12 is a schematic illustration of an adapter used by test arrangements in embodiments of the invention;

FIGS. 13A and 13B are circuit-diagram illustrations of switch configurations that may be comprised by the adapter illustrated in FIG. 12;

FIG. 14 is a flow diagram illustrating methods for testing an acoustic probe or acoustic system in accordance with embodiments of the invention;

DETAILED DESCRIPTION OF THE INVENTION

1. Introduction

Figure 1:
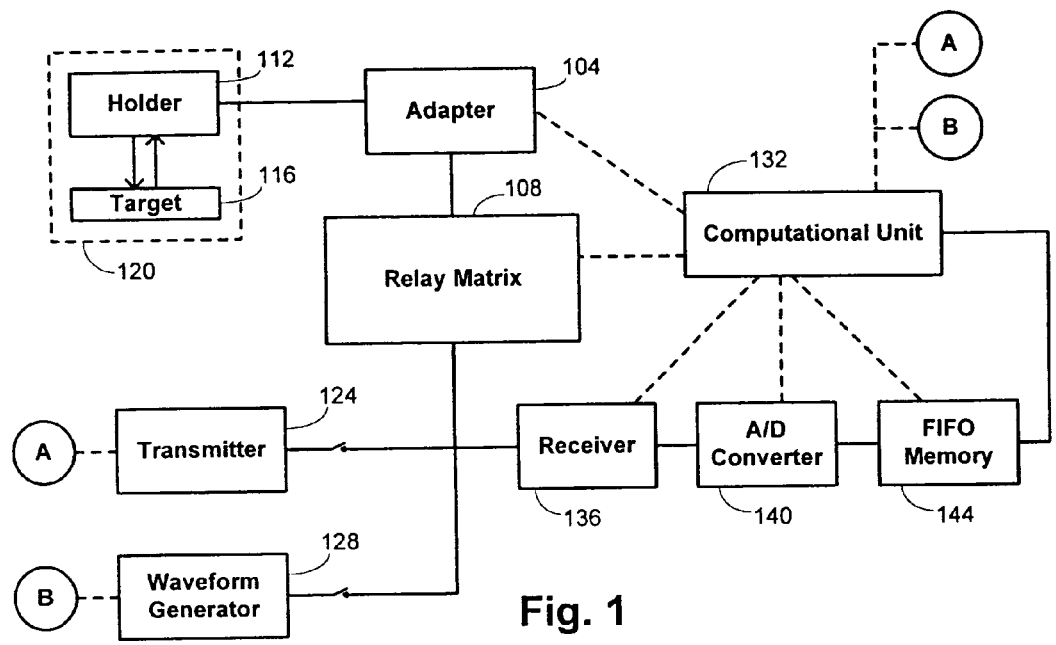
FIG. 1 is a block-diagram representation of an arrangement used for testing an acoustic probe in accordance with embodiments of the invention.

Embodiments of the invention provide apparatus and methods for testing acoustic probes and systems. Such acoustic probes and systems are sometimes referred to herein collectively as "acoustic devices." While much of the discussion below specifically discusses apparatus and methods that are suitable for testing ultrasonic probes and systems, this is intended merely for exemplary purposes and the invention is not intended to be limited by the operational frequency characteristics used by the tested probe or system. As illustrated in further detail below, each of the acoustic probes and systems that may be tested with embodiments of the invention includes a plurality of "transducer elements," which refers to elements adapted to transmit acoustic radiation and/or to receive acoustic radiation. While such elements are referred to generically herein as "transducer elements," reference is sometimes also made herein to "receiver elements" and to "transmitter elements" to distinguish them on the basis of their functions. Methods of the invention diagnose operation of the probe or system through sequential activation of the component transducer elements. In the case of a probe, such sequential activation may be initiated externally while in the case of a system, such sequential activation may use a natural operational cycling of the system.

For example, testing of an acoustic probe in embodiments of the invention may be performed by placing the probe in a test fixture in an acoustically conductive medium with a specular reflector provided at a substantially uniform distance to all of the transducer elements. Conveniently, the acoustically conductive medium may comprise water in an embodiment. The array of transducing elements comprised by the probe are then activated sequentially so that acoustic radiation is transmitted through the acoustically conductive medium towards the specular reflector. While the sequential activation may take place by activating transducing elements individually, this is not a requirement, and sequential activation may alternatively be performed simultaneously with a subset plurality of the transducing elements. Reflections from the specular reflector are digitized, and perhaps also amplified, for evaluation of the activated transducing elements. Selective activation of the transducing elements may be coordinated by a relay matrix that selectively establishes operational connections with the transducing elements.

Testing of an acoustic system in embodiments of the invention may be performed with a similar relay matrix for selectively establishing operational connections with channels comprised by the acoustic system. Connections may be established sequentially with the channels, either individually or in groups. This permits evaluation of a transmitter circuit comprised by the acoustic system as it is connected through each channel. In addition, scattering operations may be simulated electronically for each channel by transmission of an echo signal through the sequential connections. Operation of a receiver circuit comprised by the acoustic system may thus be evaluated through evaluation of image data produced by the acoustic system in response to the simulated scattering operations.

2. Acoustic-Probe Testing

An overview of embodiments of the invention suitable for testing an acoustic probe is provided with the structural diagram of FIG. 1. Testing of a probe may use signals generated by a transmitter 124. In one embodiment, such signals are generated to provide a broadband pulse that excites all of the transducer elements comprised by the probe in a substantially similar manner. For example, the signal may comprise a voltage pulse. In a particular embodiment suitable for testing many commercially available acoustic probes, the signal comprises an approximately 40-ns pulse at a magnitude of about 75 V, which provides ≥25 MHz bandwidth.

The signal generated by the transmitter 124 is routed to a selected one or subset group of the transducing elements for conversion into an acoustic signal by a relay matrix 108 and an adapter 104. In cases where a signal is routed simultaneously to a subset group of the transducing elements, the subset group may correspond to a group of neighboring transducing elements. The relay matrix 108 comprises a bidirectional switching array capable of establishing the desired connections. It is generally desirable for electrical characteristics of the relay matrix not to impact the evaluation of the transducing elements. Accordingly, an array of miniature relays may be preferred in some embodiments over semiconductor-based switching integrated circuitry to limit capacitive and resistive loads. The relays may be arranged in groups to limit the number of traces that may be active at any given time. In addition, a regular circuit topology may be used to keep the electrical load substantially constant. In one embodiment, a correction factor determined uniquely for each element may be used to further reduce measurement errors that may be associated with electrical loading associated with the relay matrix.

The relay matrix 108 may be considered to perform a mapping from one channel that corresponds to the transmitter 124 to a plurality of channels that are in communication with the adapter 104. The adapter 104 itself may be configured in accordance with characteristics of the probe to be tested, allowing connectivity between the relay matrix 108 and probes from a variety of different manufacturers. In some embodiments, the adapter 104 is configured to provide a 1:1 mapping from transducing elements of the probe to channels of the relay matrix 108. Thus, for example, if the probe has 192 transducing elements, the adapter 104 may map each of 192 channels from the relay matrix 108 to one of the transducing elements. In other embodiments described in further detail below, the adapter 104 is configured to provide different schemes for mapping channels from the relay matrix 108 to transducing elements of the probe.

Figure 2:
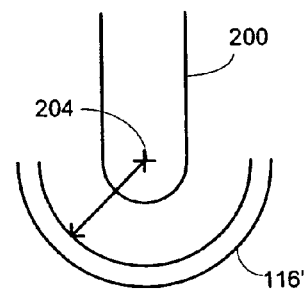
FIG. 2 is a schematic representation of a probe geometry that may be tested with embodiments of the invention.

During testing, the probe may be secured within a holder 120 adapted to maintain a fixed distance of each of the transducing elements from the acoustically reflective target 116, the assembly of holder 112 and target 116 being denoted generically with reference numeral 120. The holder 120 may also be equipped with adjustment capabilities, permitting, for example, the angular orientation of the probe to be adjusted as desired. In some instances, the reflective target 116 may comprise a flat surface, but in other instances, the shape of the target 116 may mimic a shape of the probe to compensate for positions of the transducing elements according to the probe shape. This is illustrated is FIG. 2 for a probe 200 that has a curved tip. The curvature of the probe tip is compensated for by a curvature of the reflective target 116', the curved portion of the probe tip and the reflective target 116' having a common center of curvature 204.

The transducing elements of the probe act to convert the signal generated by the transmitter 124 into an acoustic signal that is reflected from the target 116. The reflected acoustic signal is received by one of the transducing elements of the probe and converted into an electrical signal, which is routed back through the adapter 104 and relay matrix 108. The converted signal is received by a receiver 136, which may include an attenuator to reduce pulse amplitude, and transmitted to an analog-to-digital converter 140. In one embodiment the receiver has an output between 0 and 1 V and has a 1-dB bandwidth of about 10 MHz. The analog-to-digital converter 140 may advantageously be adapted to accommodate high sample rates in order to accurately sample the acoustic signals. In one embodiment, the analog-to-digital converter 140 is adapted to accommodate sample rates of at least 100 MHz. At such a rate, at least ten samples may be retrieved per cycle on a 10-MHz probe. In some instances, the analog-to-digital converter 140 may additionally include a video-frame-capture capability to permit capturing of an ultrasonic image for further use as described below. The output of the analog-to-digital converter 140 is routed to a computational unit 132 for analysis and/or display, in some instances through an intermediary first-in-first-out ("FIFO") memory 144 to account for the high speed of the analog-to-digital converter 140.

The computational unit 132 may comprise any device having processing capability sufficient to analyze data received from the analog-to-digital converter 140 in accordance with embodiments of the invention. For example, the computational unit 132 may comprise a personal computer, a mainframe, or a laptop, whose mobility makes it especially convenient. The dashed lines in FIG. 1 illustrate that, in addition to receiving data for analysis, the computational unit 132 may be configured to control each of the components comprised by the testing apparatus.

Figure 3:
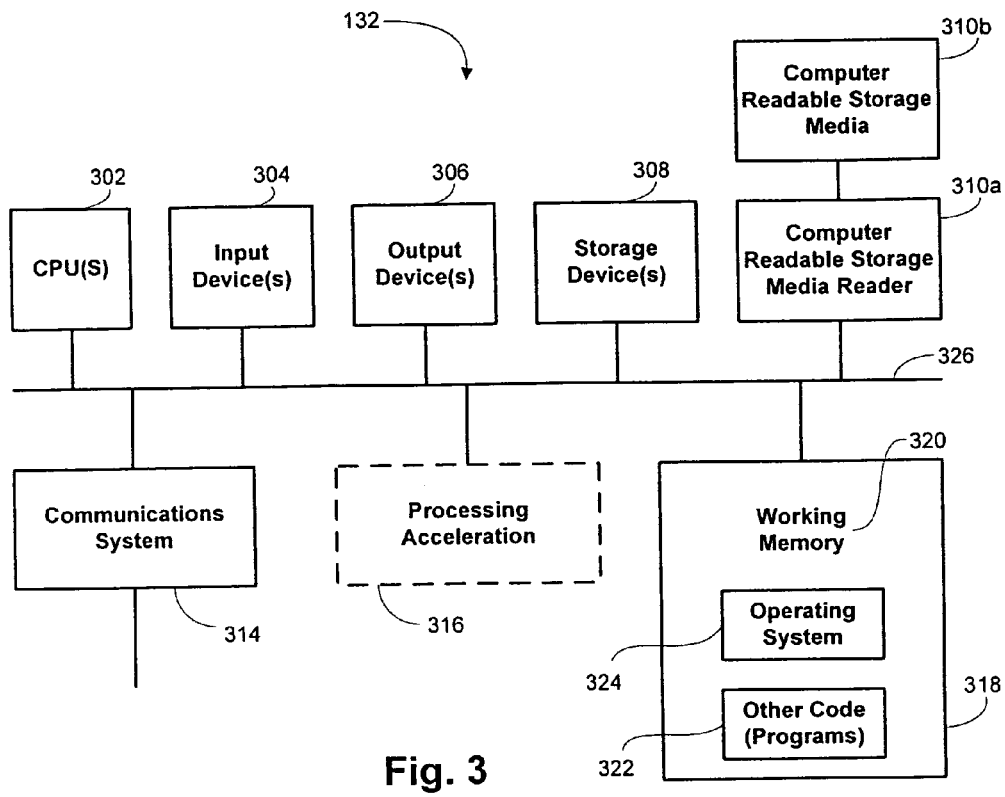
FIG. 3 is a block-diagram representation of a computational unit on which methods of the invention may be embodied.

FIG. 3 provides a schematic illustration of a structural arrangement that may be used to implement the computational unit 132. FIG. 3 broadly illustrates how individual elements of the computational unit 132 may be implemented in a separated or more integrated manner. The computational unit 132 is shown comprised of hardware elements that are electrically coupled via bus 326, including a processor 302, an input device 304, an output device 306, a storage device 308, a computer-readable storage media reader 310a, a communications system 314, a processing acceleration unit 316 such as a DSP or special-purpose processor, and a memory 318. The computer-readable storage media reader 310a is further connected to a computer-readable storage medium 310b, the combination comprehensively representing remote, local, fixed, and/or removable storage devices plus storage media for temporarily and/or more permanently containing computer-readable information. The communications system 314 may comprise a wired, wireless, modem, and/or other type of interfacing connection and permits data to be exchanged with external devices as desired.

The computational unit 132 also comprises software elements, shown as being currently located within working memory 320, including an operating system 324 and other code 322, such as a program designed to implement methods of the invention. It will be apparent to those skilled in the art that substantial variations may be made in accordance with specific requirements. For example, customized hardware might also be used and/or particular elements might be implemented in hardware, software (including portable software, such as applets), or both. Further, connection to other computing devices such as network input/output devices may be employed. Connections between the computational unit 132 and the various components of the testing apparatus may use any suitable connection, such as a parallel-port connection, a universal-serial-bus ("USB") connection, and the like.

Figure 4:
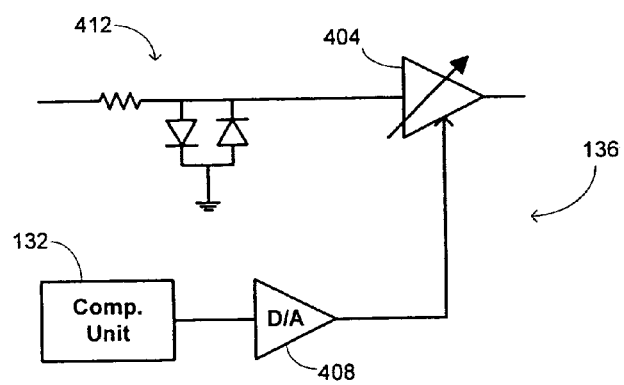
FIG. 4 is a circuit diagram illustrating a receiver unit used in embodiments of the invention.

An explicit example of a circuit structure that may be used for the receiver 136 in one embodiment is illustrated in FIG. 4. In this example, the receiver 136 comprises an attenuator 412 to reduce pulse amplitude and provide input protection for the receiver as well as a variable-gain amplifier 404. A typical range for the variable-gain amplifier 404 may be −20 to +60 dB, although a narrower range, such as +6 to +30 dB may be adequate for testing many commercially available probes. The variable-gain amplifier 404 may be controlled by the computational unit 132, with a digital-to-analog converter 408 being used to convert instructions from the computational unit 132. In one embodiment, the variable-gain amplifier 404 is configured such that a linear change in voltage corresponds to a logarithmic change in gain.

The configuration described in connection with FIGS. 1–4 is sufficient in many instances to permit a diagnosis of transducing-element operation in acoustic probes. For example, receipt of a signal during cycling through the transducer elements when correlated with a time of interrogation indicates that a specific element is functioning correctly, while failure to receive a signal indicates that that element is not functioning correctly. In several embodiments, this information is augmented by analyzing the capacitance of elements in the system to provide additional useful diagnostic information. The capacitance analyses make use of a waveform generator 128, also shown in FIG. 1 as being under the control of the computational unit 132.

Figure 5A:
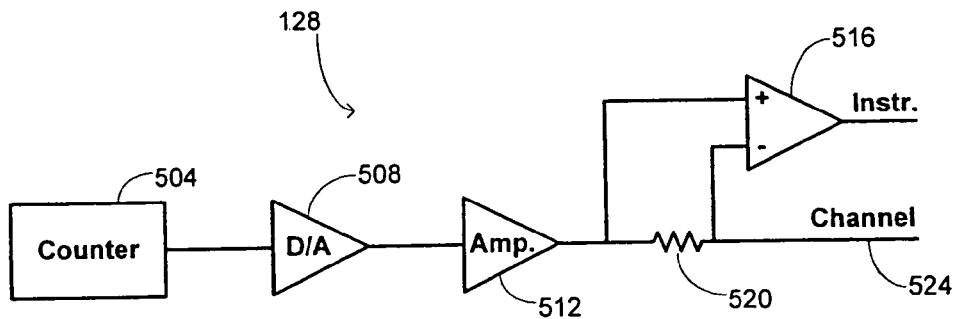
FIG. 5A is a circuit diagram illustrating a capacitance circuit used in embodiments of the invention.

A circuit structure of the waveform generator 128 is illustrated for a particular embodiment in FIG. 5A. A waveform is generated digitally by a counter 504, with the waveform having a variation in voltage $\Delta V$ over time $\Delta t$, thereby defining a capacitance $$C \equiv \frac{i}{(\Delta V / \Delta t)}.$$

Figure 5B:
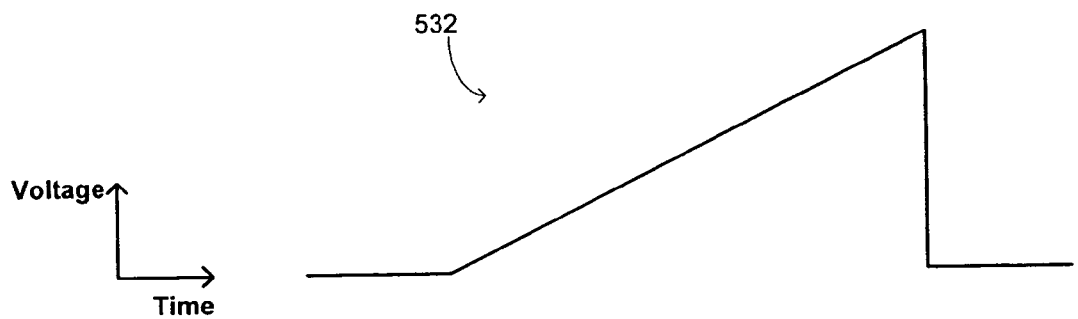
FIG. 5B illustrates a ramp profile for a pulse used by the waveform generator of FIG. 5A.

The waveform is converted with a digital-to-analog converter 508 and amplified with an amplifier 512. The waveform is transmitted onto the channel 524 that feeds to the relay matrix with a source resistance 520 used to drive the probe and with an instrumentation amplifier 516. A suitable value for the source resistance 520 in a particular embodiment is approximately 10 k$\Omega$. While the invention is not limited to a specific shape for the capacitance-defining waveform, it may conveniently take the form of a linear ramp function 532 such as shown in FIG. 5B, thereby providing a constant capacitance. Merely by way of example, the voltage increase of the waveform could be $\Delta V$=4.096 V over a time period of $\Delta t$=409.6 µs, thereby providing a capacitance of $C=i/10^4$ F.

For the simplest probe structure, the capacitance of each of the transducing elements may thus be determined during interrogation of that element by generating the waveform and measuring the resulting current i. In some instances, this method may be complicated by a probe structure that provides an additional significant source of capacitance. In particular, each transducing element may comprise a piezoelectric crystal used to perform electrical-acoustic conversions. The probe may supply energy to each such piezoelectric crystal with a coaxial cable that has an intrinsically high capacitance. Accordingly, such probe manufacturers often use a tuning circuit to tune out the capacitance of the coaxial cable and thereby permit effective energy coupling into the piezoelectric crystal. Any suitable tuning circuit known to those of skill in the art may be used, such as with a standard second-order tuned circuit. The tuning circuit typically comprises an inductive element, which may be provided in series or in parallel with the piezoelectric crystal. Methods of the invention may account for the specific configuration of the tuning circuit in different embodiments.

Figure 6A:
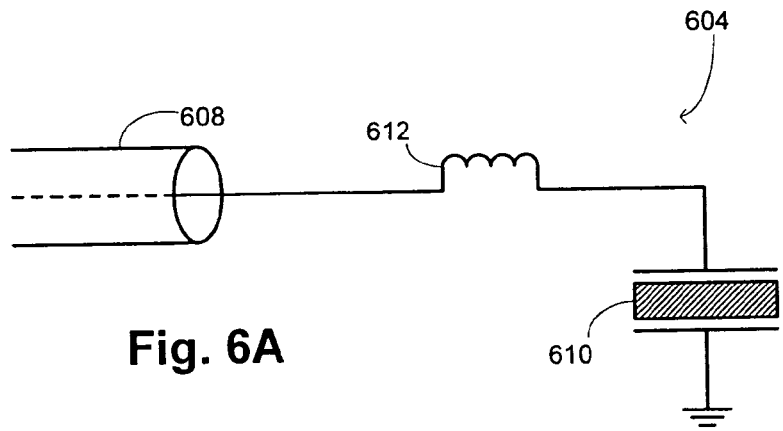
FIGS. 6A and 6B illustrate series and parallel tuning arrangements of an acoustic probe.

The electrical structure of a series-inductor tuned probe 604 is illustrated in FIG. 6A. Energy is coupled into the piezoelectric crystal 610 comprised by each transducing element with a coaxial cable 608. The circuit for tuning out the capacitance of the coaxial cable 608 comprises an inductive element 612 provided in series with the piezoelectric crystal 610, and may also include a resistive element (not shown), usually provided in parallel with the piezoelectric crystal 610. Testing of such a series-inductor tuned probe 604 may thus be performed in a manner similar to that used for an untuned probe. In particular, the waveform generator 128 may provide a low-frequency waveform, i.e. such as on the order of less than 10 kHz or less than 100 kHz depending on the embodiment, and the resulting current i measured. The capacitance is then determined from the ratio of the current i to the time rate of change of voltage in the waveform.

Figure 6B:
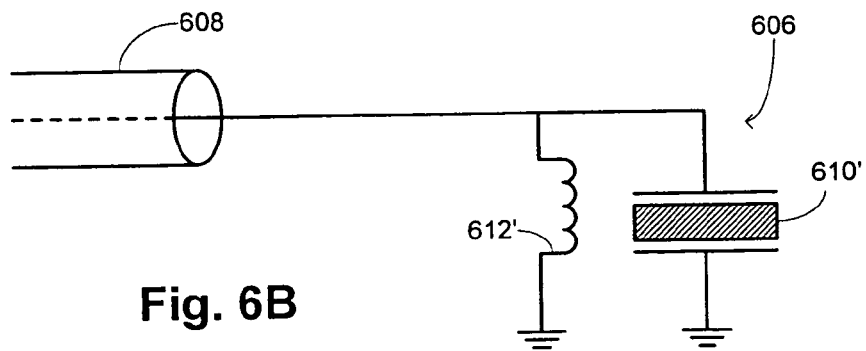

Use of such a low-frequency waveform may be less effective for a parallel-inductor tuned probe 606 such as illustrated in FIG. 6B. In this instance, the tuning circuit comprises an inductive element 612' provided in parallel with the piezoelectric crystal 610', and may also include a resistive element (not shown), usually also provided in parallel with the piezoelectric crystal 610'. With such an arrangement, a low-frequency waveform on the order of less than 100 kHz results in a small inductive reactance. Accordingly, in some embodiments, a higher frequency is used for the waveform. This frequency is chosen to be outside the active range of the piezoelectric crystal to avoid spuriously interfering with the operation of the probe, such as below a resonant-frequency range of the piezoelectric crystal. For example, if the piezoelectric crystal has a resonant frequency in the range of 2–10 MHz, which is common for ultrasonic applications, the frequency of the waveform may be in the range of 0.5–1.5 MHz, such as at approximately 1.25 MHz.

Figure 7:
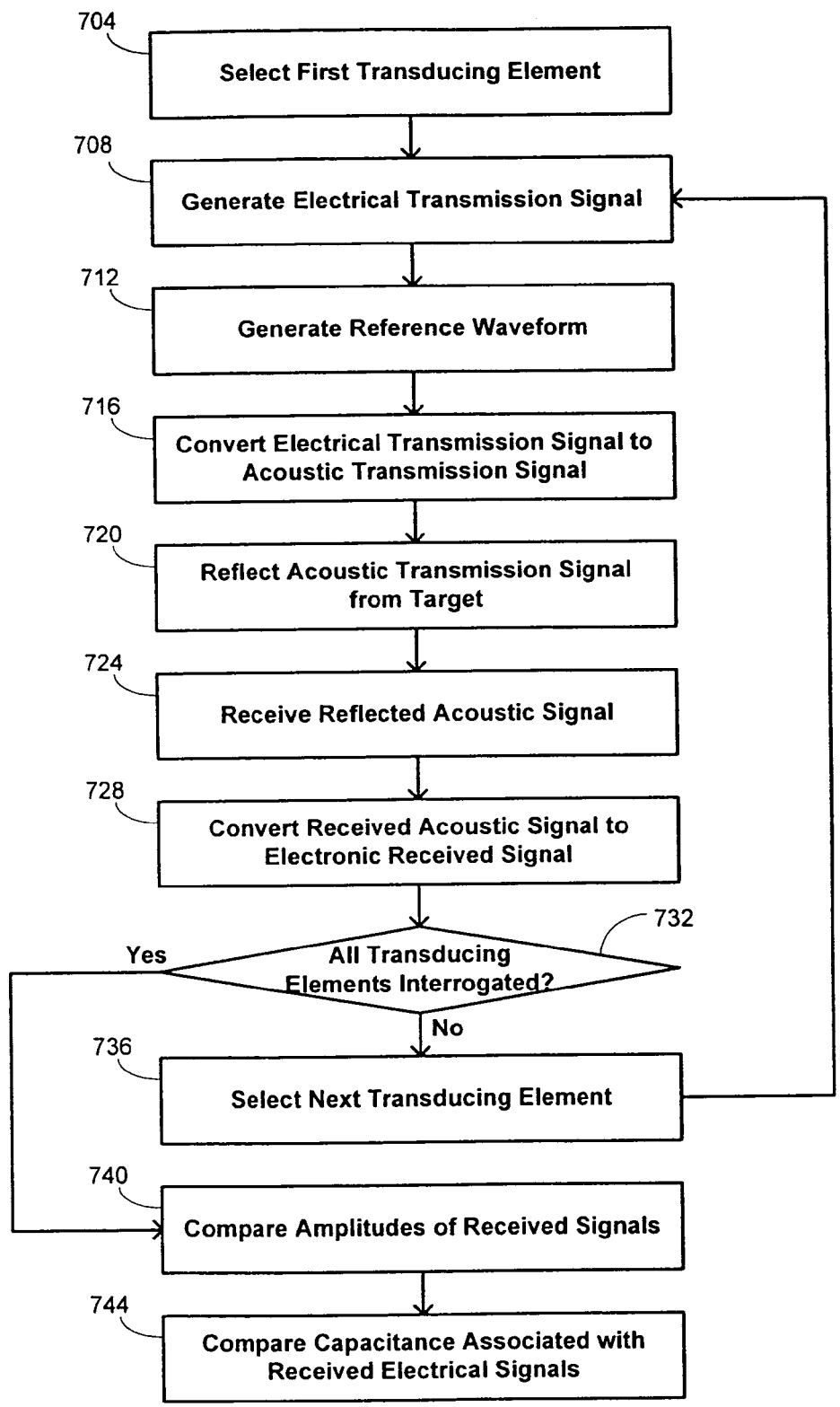
FIG. 7 is a flow diagram illustrating methods for testing an acoustic probe in accordance with embodiments of the invention.

Methods that may be used by the arrangements described in connection with FIGS. 1–6B to test the operation of a probe are thus summarized with the flow diagram of FIG. 7. While the flow diagram is provided with a specific ordering, it will be appreciated that there is no requirement that this ordering be followed. In alternative embodiments, functions may be performed simultaneously even if they are shown separately in FIG. 7, and may be performed in a different order than the specific example shown in FIG. 7. At block 704, the method begins by selecting a first transducer of the probe to be interrogated. The selected transducer may be selected according to a routing defined by the relay matrix 108 and coupled operationally to the selected transducing elements through the adapter 104. This routing is used to transmit an electrical transmission signal generated at block 708 and a reference waveform generated at block 712 to the selected transducing element. The transducing element acts to convert the electrical transmission signal to an acoustic transmission signal at block 716. After the acoustic transmission signal is reflected from the target at block 720 and received at block 724, it is converted to an electrical received signal.

This same procedure is performed sequentially for each of the transducing elements. This is indicated at blocks 732 and 736 where a check is made whether all transducing elements have been interrogated, and the next transducing element being selected if they have not been. Once interrogation of all the transducing elements comprised by the probe has been completed, the collected data are analyzed to diagnose whether any of the transducing elements is failing to operate within normal parameters. A comparison of the amplitudes of the received signals at block 740 provides a broad measure of whether there is a defect associated with any of the transducing elements; this is usually indicated by lack of a received signal, which identifies a corresponding defect, although a substantially reduced amplitude may also provide a similar indication.

More detailed diagnostic information is provided by a comparison of capacitance associated with the interrogation of each of the transducing elements with the reference waveform, as performed at block 744. The diagnostic value of such capacitance determinations may be illustrated with some examples, which are provided herein merely for illustrative purposes and are not intended to limit the scope of the invention; other diagnostic capabilities resulting from the capacitance determinations will be evident to those of skill in the art after reading this description.

Figure 8:
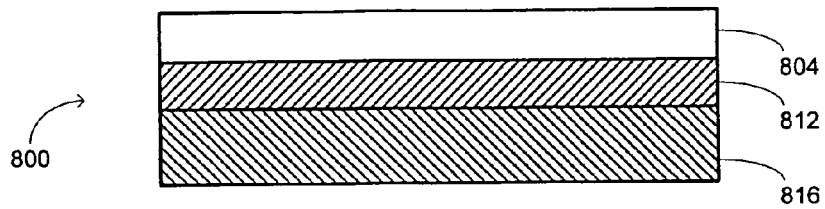
FIG. 8 is a schematic representation of an acoustic element that may be diagnosed in accordance with embodiments of the invention.

A first example may be understood with reference to FIG. 8, which provides a schematic illustration of a structure that may be used for one of the transducing elements 800. The transducing element comprises a backing 816 over which the piezoelectric crystal 812 is provided. An acoustic lens 804 provided over the piezoelectric crystal 812 provides electrical isolation of the piezoelectric crystal 812 and acoustic impedance matching. A defect in the operation of the transducing element 800 may result from different types of conditions that may be discriminated by the capacitance determinations. For example, the defect may result from delamination of the acoustic lens 804 from the piezoelectric crystal 812. This condition is manifested by lack of an electrical received signal concomitant with substantial matching of the capacitance of the particular transducing element with the capacitance of fully functioning transducing elements. The defect may alternatively result from cracking or other damage to the piezoelectric crystal 812. This condition is manifested by lack of an electrical received signal concomitant with a failure of the capacitance of the particular transducing element to match the capacitance of fully functioning transducing elements.

In another example, the capacitance determinations may be used to identify defects associated with the coaxial cables used to couple energy to the respective piezoelectric crystals. The capacitance determination is a particularly useful discriminant for such defects because it is approximately proportional to the distance along the cable where the defect occurs. Thus, if interrogation of a particular transducing element results in no capacitance, the respective cable may not be connected with that transducing element. If interrogation of that transducing element results in a capacitance that is half what is otherwise expected for a properly functioning transducing element, the respective cable may be broken or otherwise damaged approximately halfway along the length of the cable.

3. Acoustic-System Testing

Figure 9:
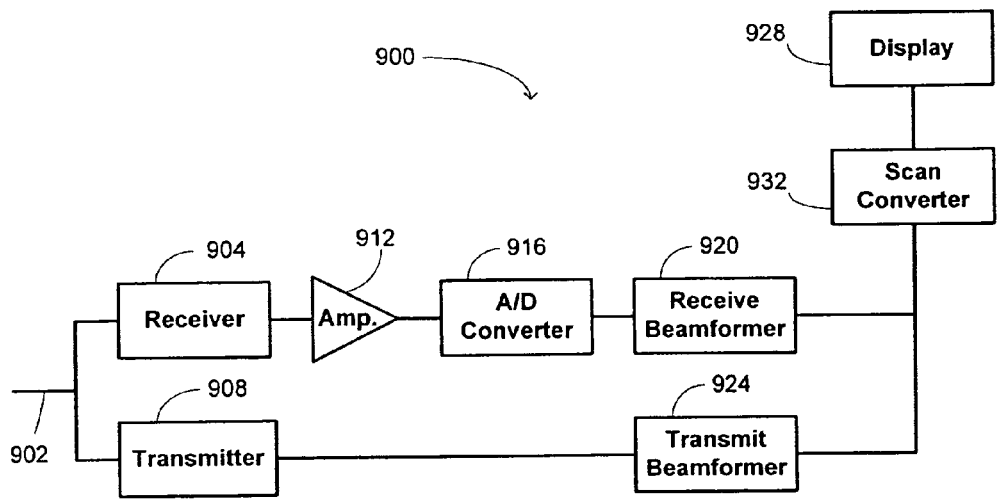
FIG. 9 is a block-diagram representation of an acoustic system that may be tested in accordance with embodiments of the invention.

Embodiments of the invention may be used for testing the operation of a variety of different acoustic systems. These embodiments are illustrated with a type of acoustic system shown schematically with the structural diagram of FIG. 9, although it will be evident to those of skill in the art after reading this description that the methods and apparatus of the invention may alternatively be used for operational diagnosis of other types of acoustic systems. The components shown for the acoustic-system structure in FIG. 9 are shared by a large number of different acoustic systems, although specific systems may have these components organized differently.

The acoustic system 900 includes a multichannel interface 902 that is in communication with receiver 904 and transmitter 908 components. The receiver 904 and transmitter 908 are configured for conversion between electrical and acoustic signals so that investigation of an object may be performed by irradiating the object with the acoustic signals but performing analysis with the electrical signals. Thus, the receiver 904 may include components that convert acoustic signals to electrical signals while the transmitter 908 may conversely include components that convert electrical signals to acoustic signals. Generally, each of the receiver 904 and transmitter 908 are configured with multichannel capacity. The receiver 904 may be provided in communication with an amplifier 912 and analog-to-digital converter 916 to accommodate acoustic signals that may be attenuated after scattering by the object by amplifying and digitizing the converted electrical signals. Thus, after digitization, differences between the received and transmitted electrical signals provide information derived from scattering of the corresponding acoustic signals from the object.

The multichannel information provided from the multichannel interface 902 is accommodated by a receive beamformer 920 and a transmit beamformer 924, each of which is respectively configured for adding contributions from a plurality of elements comprised by the receiver and transmitter elements 904 and 908. The receive and transmit beamformers 920 and 924 include array phasing capability to be applied respectively for the received and transmitted signals. The acoustic system 900 may include a capacity for displaying an image, which is typically viewed by an operator trained in evaluating acoustic images so that features of interest in the object, such as medical pathologies in an organ, may be identified. The image is generated by a scan converter 932 provided in communication with the receive and transmit beamformers 920 and 924 and transmitted to a display 928 for rendering.

Figure 10:
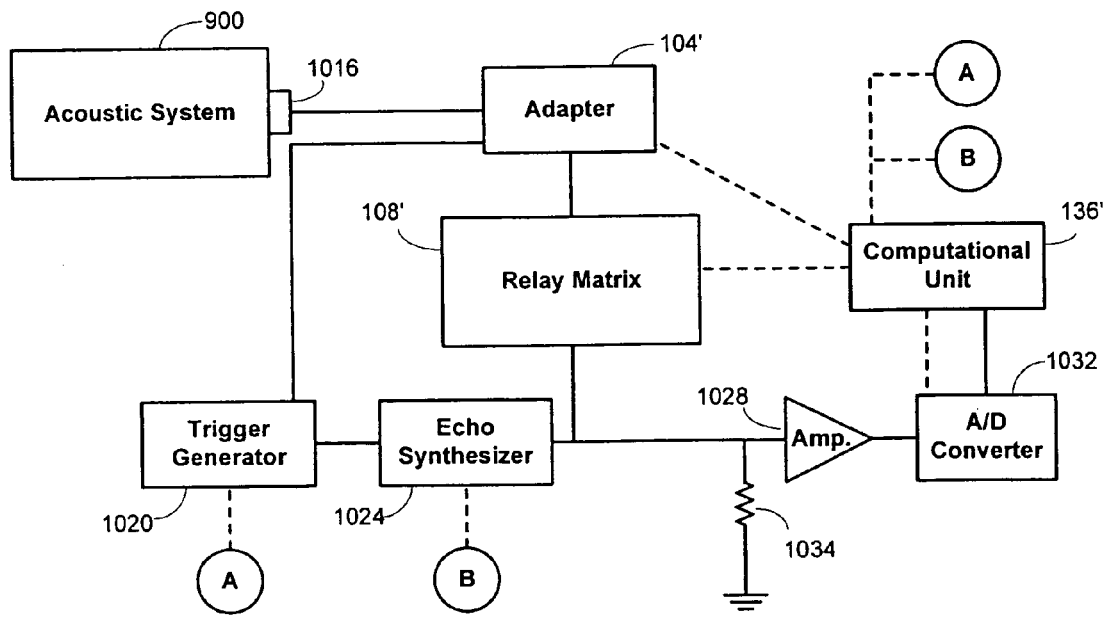
FIG. 10 is a block-diagram representation of an arrangement used for testing an acoustic system in accordance with embodiments of the invention.

The testing methods and apparatus provided by embodiments of the invention may be used to diagnose the operational behavior of acoustic systems such as that described in connection with FIG. 9. In particular, embodiments of the invention permit defects to be identified in the operation of individual receiver and transmitter elements. Such defects are often not immediately apparent in the image provided on the display 928 because the image is derived from multiple elements. Nevertheless, the absence of information from a defective element may result in subtle distortions of the image that may lead to incorrect analyses of the object under study. An overview of embodiments of the invention suitable for testing the acoustic system 900 is provided with the structural diagram of FIG. 10. Similar to the apparatus used for acoustic-probe testing, the acoustic-system testing apparatus includes a relay matrix 108' adapted to perform signal mapping from one channel to a plurality of channels in communication with an adapter 104'. For interrogation of channels within the system, a multichannel connection interface 1016 may be provided between the adapter 104' and the acoustic system 900.

In one embodiment, the natural cycling of the acoustic system 900 through its multiple channels is used to evaluate operation of transmitter elements. Signals generated by elements of the transmitter 908 are collected by the adapter 104' through the connection interface 1016 and provided to the relay matrix 108'. The relay matrix 108' is configured for discrimination of individual channels received from the adapter 104' in the same manner described above for probe testing. Signal corresponding to the selected channels are provided to an analog-to-digital converter 1032, perhaps after attenuation and/or amplification by an attenuator 1034 and/or amplifier 1028. The digitized signals are provided to a computational unit 136', which thus systematically identifies whether a signal has been received from each of the transmitter elements comprised by the acoustic system 900.

In another embodiment, operation of the receiver elements may be evaluated by providing synthesized echo information back into the acoustic system 900. In response to a transmit signal received by the adapter 104' from the acoustic system 900 through the connection interface 1016, a trigger generator 1020 activates an echo synthesizer 1024, which generates a signal to be routed back into the acoustic system 900 for receipt by the receiver 904. Specific channels corresponding to different elements comprised by the receiver 904 are selected according to a configuration of the relay matrix 108' and the echo signal output from the relay matrix 108' is transmitted with the adapter 104' to the acoustic system 900. In this way, the echo signal is directed to a specific element comprised by the receiver 904, causing a dot to be displayed on the display 928 for each beam that that element is used on. A defective channel may thus be characterized by the absence of an expected line on the display. Such absence may be identified by a human operator, although in other embodiments a frame-capture device is interfaced with the video output to detect the presence or absence of lines automatically. In an alternative embodiment, Doppler information may be analyzed to identify defective channels. The relay matrix 108' may be cycled through each of the channels corresponding to all elements comprised by the receiver 904 to evaluate the operation of each of those elements. The components of the acoustic-system testing apparatus may be controlled by a computational unit 136' in a similar fashion to the control provided for the acoustic-probe testing apparatus.

Figure 11A:
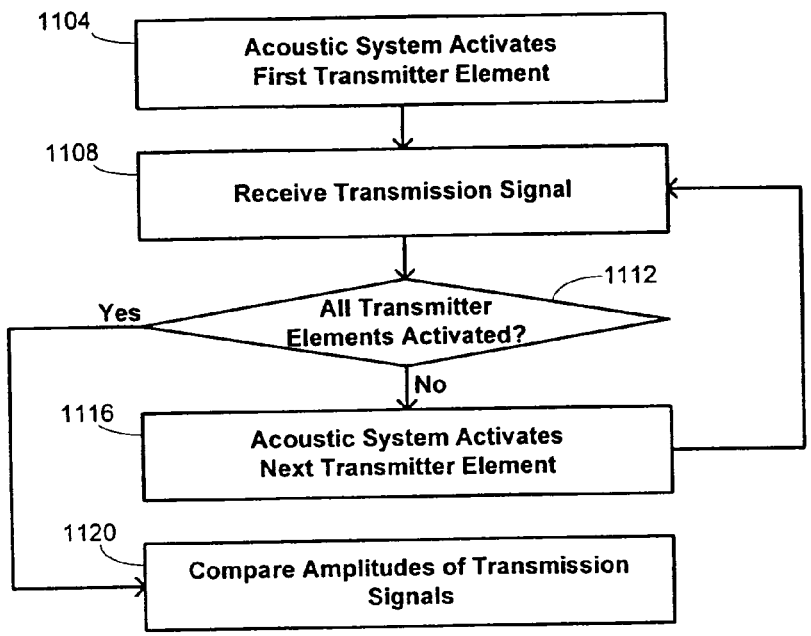
FIGS. 11A and 11B are flow diagrams illustrating methods for testing an acoustic system in accordance with embodiments of the invention.
Figure 11B:
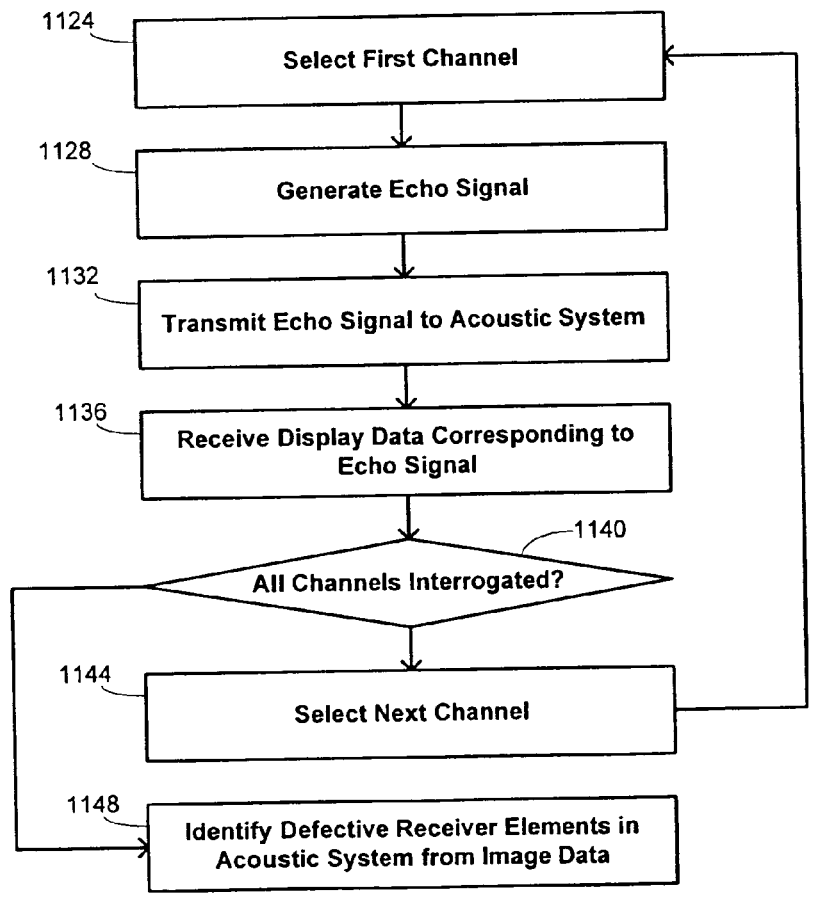

FIGS. 11A and 11B thus provide flow diagrams to summarize methods that may be used for testing an acoustic system in accordance with embodiments of the invention. FIG. 11A provides a flow diagram for testing operation of a transmitter comprised by the acoustic system by using the natural cycling of the acoustic system through different transmission channels. Thus, at block 1104, the acoustic system activates a first of a plurality of transmitter elements comprised by the transmitter as part of such cycling. At block 1108, the transmission signal generated by the activated transmitter element is received. A check is made at block 1112 whether all of the transmitter elements have been activated, i.e. whether a full cycle of the acoustic system has been completed. If not, the method waits for the acoustic system to activate the next transmitter element at block 1116 so that the transmission signal for that transmitter element may be received. After at least one full cycle has been completed, a comparison is performed of the amplitude of the different transmission signals. Absence of a signal or other significant deviation of the amplitude of the signal from the amplitude of the other signals is indicative of a defect associated with the corresponding transmitter element.

FIG. 11B provides a flow diagram for testing operation of a receiver comprised by the acoustic system by using the echo-synthesis components described above. In this instance, systematic interrogation of channels in the acoustic system is coordinated externally. Thus, at block 1124, the first channel to be interrogated is selected. An echo signal is generated at block 1128 and transmitted to the acoustic system at block 1132. Display data corresponding to the echo signal is captured at block 1136, with the method looping as indicated at blocks 1140 and 1144 until all channels have been interrogated. At block 1148, defective receiver elements are identified from image data generated by the acoustic system, such as by identifying the presence or absence in the image data of lines corresponding to specific receiver elements.

In some embodiments, a capacitance analysis may be added to the methods described above for testing an acoustic system. Such an analysis may be performed in a manner similar to that described above for acoustic-probe testing by configuring a waveform generator to supply a waveform that may be used to determine the capacitance of the transmitter and/or receiver elements. Knowledge of the capacitance may be used as described above to limit the type of defect identified more narrowly.

4. Adapter Configurations

There are a variety of different adapter configurations that may be used in different embodiments of the invention, some of which are described in detail herein. According to one embodiment, illustrated in FIG. 12, the adapter 104" includes internal switching capability in the form of an internal N-channel switch 1204. Inclusion of such capacity provides an economical way of increasing the channel capability of the testing apparatus.

Merely by way of example, consider the case where the testing apparatus is to be used to test a 192-channel probe or system. In such instances, interfacing the 192 channels through the adapter with the relay matrix 108" may be accomplished with, say, a 260-pin zero-insertion force ("ZIF") connector 1208. Such connectors are readily available commercially at reasonable cost and have sufficient numbers of pins to accommodate the 192 channels as well as power connections, ground connections, computer connections, and the like. If the testing apparatus is then to be used to test a 256-channel probe or system, the capacity of the connector 1208 is insufficient. Replacement of the 260-pin ZIF connector with a larger connector greatly increases the overall cost of the apparatus and makes inventory control difficult because such larger connectors are considerably more costly and have poor distribution availability.

These disadvantages are avoided by including the N-channel switch 1204 in the adapter. Referring again to the example above, a 256-channel probe or system may be tested with the apparatus even with a 260-pin ZIF connector 1208 since some of the mapping of channels may be performed by a 64-channel switch 1204. In the case of a probe test, the imposed interrogation channel may be selected by a combination of routing through the relay matrix 108" and the N-channel switch 1204. In the case of a system test, use of the natural system cycling may similarly be accommodated by a combination of routing through the relay matrix 108" and the N-channel switch 1204.

There are a variety of configurations that may be used to implement the N-channel switch 1204. For example, FIG. 13A illustrates an embodiment in which a plurality N of single-channel switches are used directly to implement the N-channel switch 1304, with one terminal of each of the single-channel switches being connected together electrically. In another embodiment, illustrated in FIG. 13B, single-channel switches are electrically connected in a tree arrangement to form the N-channel switch 1308. The tree arrangement defines banks of single-channel switches such that at any time no more that one bank is active. For example, banks may be provided that have only sixteen, eight, or some other appropriate number of single-channel switches. Although the total number of single-channel switches in such an embodiment may be greater than N, this configuration limits the capacitance associated with the adapter 104, which might otherwise interfere with the capability of the testing apparatus to make accurate measurements. The tree arrangement is thus particularly useful in embodiments where capacitance determinations are used as part of the acoustic probe or system diagnosis.

FIG. 14 provides a flow diagram that summarizes how use of an adapter comprising an N-channel switch may be integrated into a method for testing an acoustic probe; it will be evident to those of skill in the art that it may similarly be integrated into a method for testing an acoustic system. In this embodiment, the adapter 104″ may substitute for the adapter 104 in FIG. 1. At block 1404, a first channel is selected for interrogation. The electrical transmission signal to be used for the interrogation is generated at block 1408. The electrical transmission signal is routed to the selected channel through a combination routings through a relay matrix and a switch in the adapter respectively at blocks 1410 and 1412. A transducing element comprised by the acoustic probe that corresponds to the selected channel converts the electrical transmission signal to an acoustic transmission signal at block 1416. After the acoustic transmission signal has been reflected from a target at block 1420, it is received at block 1424 and converted to an electrical received signal at block 1428. Data are collected in this manner by interrogating all channels of the probe, as indicated with the looping blocks 1432 and 1436, so that a comparison may be made of the relative amplitudes of the received signals at block 1440 to analyze the operation of the probe as described above. The order of the blocks presented in FIG. 14 is intended to be exemplary and not limiting; other orders for the functions described may alternatively be used without exceeding the intended scope of the invention. Furthermore, other diagnostic aspects may be incorporated into the method described with respect to FIG. 14, such as the use of capacitance determinations described previously.

Figure 15:
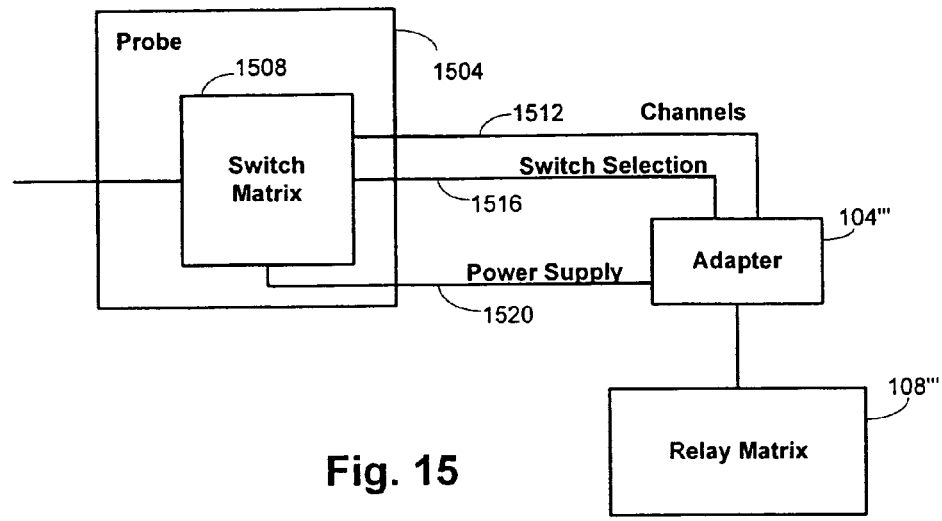
FIG. 15 is a block-diagram illustration of an arrangement used for testing a multiplexing acoustic probe in accordance with embodiments of the invention.

In another embodiment, an adapter may be provided for methods and apparatus used in testing a multiplexing acoustic probe. As used herein, a "multiplexing acoustic probe" refers to an acoustic probe that is equipped with internal switching capability to allow the probe itself to map a greater number of transducing elements on the probe to a smaller number of channels. Such a multiplexing capability permits the internal switching capability to act as a surrogate for a larger number of channels that need be accommodated on a nonmultiplexing acoustic probe with the same element capacity. The structure of such a probe is illustrated schematically in FIG. 15, which shows more generally how embodiments of the invention may be used to test the operation of such a probe.

The multiplexing acoustic probe 1504 includes a switch matrix 1508 that performs the mapping from the input channels onto the greater number of transducing elements. In addition to an interface 1512 for communicating information over the input channels between the switch matrix 1508 and an adapter 104‴, interfaces 1516 and 1520 may be included for providing switch-selection information from the adapter 104‴ to the switch matrix 1508 and for providing power from the adapter 104‴ to the switch matrix 1508. As in other embodiments, the adapter 104‴ is provided in communication with a relay matrix 108‴ configured to route signals selectively to perform methods of the invention. While for convenience only the adapter 104‴ and relay matrix 108‴ are explicitly shown in FIG. 15, the apparatus may additionally include other components described in connection with FIG. 1.

Figure 16:
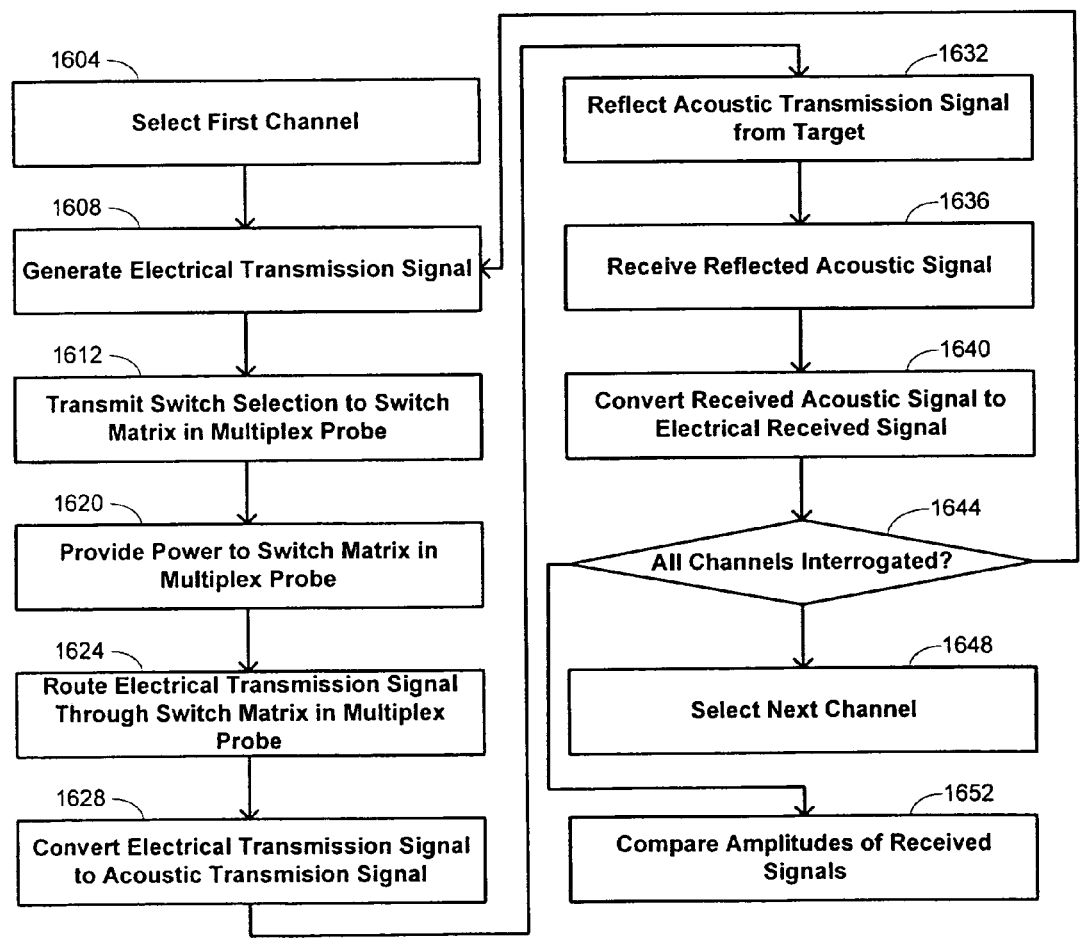
FIG. 16 is a flow diagram illustrating methods for testing a multiplexing acoustic probe in accordance with embodiments of the invention.

FIG. 16 provides a flow diagram illustrating a method for testing a multiplexing acoustic probe in accordance with an embodiment. At block 1604, a first transducing element comprised by the multiplexing acoustic probe is selected for interrogation. The electrical transmission signal to be used for the interrogation is generated at block 1608, and is routed to the selected transducing element. Such routing may be performed in part by the relay matrix 108‴ and in part by the adapter 104‴ if it is equipped with internal switching capability. In addition, the routing to the selected transducing element is performed at least in part by the switch matrix 1508. This may include transmitting switch-selection information to the switch matrix 1508 at block 1612, providing power to the switch matrix 1508 at block 1620, and then routing the electrical transmission signal through the switch matrix 1508 at block 1624. The selected transducing element responds to the electrical transmission signals by converting it to an acoustic signal at block 1628 that may be reflected from a target at block 1632. After receiving the reflected acoustic signal at block 1636, it is converted to an electrical received signal at block 1640. This technique is used to collect data corresponding to all the transducing elements of the multiplexing acoustic probe, as indicated by blocks 1644 and 1648, allowing a comparison of relative amplitudes to be made at block 1652 to analyze the functionality of the transducing elements. The functions illustrated in FIG. 16 are not exhaustive, nor is the order in which they are presented necessary. For example, other diagnostic aspects may be incorporated, such as the use of capacitance determinations described previously, and the order of the functions may be changed without exceeding the intended scope of the invention.

It is evident that the methods and apparatus described above provide specific information regarding the characteristics and behavior of individual acoustic probes that may be collected by the computational unit. This information may be used to define a probe-identification catalog so that automatic probe identification is performed when the apparatus is connected with the probe.

Having described several embodiments, it will be recognized by those of skill in the art that various modifications, alternative constructions, and equivalents may be used without departing from the spirit of the invention. Accordingly, the above description should not be taken as limiting the scope of the invention, which is defined in the following claims.

What is claimed is:

1. Apparatus for testing an acoustic device having a plurality of transducing elements adapted for conversion between acoustic and electrical signals, the apparatus comprising:

a transmitter adapted to generate an electrical transmission signal;

a relay element adapted to route the electrical transmission signal to a selected transducing element;

a receiver adapted to receive an electrical received signal from the acoustic device;

a waveform generator adapted to generate a reference signal with which a capacitance associated with the selected transducing element may be determine; and an adapter adapted to interface between the relay element and the transducing elements, the adapter having a multichannel switch.

2. The apparatus recited in claim 1 further comprising a computational unit configured to diagnose operational characteristics of the selected transducing element from the determined capacitance and the electrical received signal.

3. The apparatus recited in claim 1 wherein the electrical received signal corresponds to an acoustic signal converted from the electrical transmission signal and reflected from a target.

4. The apparatus recited in claim 1 wherein the transmitter is adapted to generate the electrical transmission signal in the form of a voltage pulse.

5. The apparatus recited in claim 1 wherein the waveform generator is adapted to generate the reference signal in the form of a linear voltage ramp signal.

6. The apparatus recited in claim 1 wherein:
the selected transducing element comprises a piezoelectric crystal; and
the waveform generator is adapted to generate the reference signal with a frequency less than a resonant frequency of the piezoelectric crystal.

7. The apparatus recited in claim 1 wherein the selected transducing element comprises a plurality of selected transducing elements.

8. A computer-readable storage medium having a computer-readable program embodied therein for directing operation of an apparatus including a transmitter, a relay element, a receiver, a waveform generator, an adapter having a multichannel switch, and a computational unit, wherein the computer-readable program includes instructions for operating the apparatus to test an acoustic device having a plurality of transducing elements adapted for conversion between acoustic and electrical signals in accordance with the following:
generating with the transmitter an electrical transmission signal;
transmitting with the relay element the electrical transmission signal to a selected transducing element;
receiving with the receiver an electrical received signal from the acoustic device;
generating with the waveform generator a reference signal with which a capacitance associated with the selected transducing element may be determined;
diagnosing with the computational unit operational characteristics of the selected transducing element from the determined capacitance and the electrical received signal; and
transmitting the electrical transmission signal through the adapter.

9. The computer-readable storage medium recited in claim 8 wherein the computer-readable program includes instructions for generating the electrical transmission signal in the form of a voltage pulse.

10. The computer-readable storage medium recited in claim 8 wherein the computer-readable program includes instructions for generating the reference signal in the from of a linear voltage ramp signal.

11. The computer-readable storage medium recited in claim 8 wherein:
the selected transducing element comprises a cable connection, the capacitance deriving at least in part from a cable capacitance of the cable connection; and
the computer-readable program includes instructions for diagnosing operational characteristics by determining that the capacitance arising from the cable capacitance is a fraction of an expected value.

12. The computer-readable storage medium recited in claim 8 wherein the computer-readable program includes instructions for diagnosing the operational characteristics by:
determining that an amplitude of the electrical received signal is substantially zero; and
determining whether the capacitance is consistent with an expected value.

* * * * *